(12) United States Patent
Kim et al.

(10) Patent No.: US 6,545,763 B1
(45) Date of Patent: Apr. 8, 2003

(54) METHOD FOR MEASURING A THICKNESS PROFILE AND A REFRACTIVE INDEX USING WHITE-LIGHT SCANNING INTERFEROMETRY AND RECORDING MEDIUM THEREFOR

(75) Inventors: Seung Woo Kim, Taejun (KR); Gee Hong Kim, Taejun (KR)

(73) Assignee: Korea Advanced Institute of Science and Technology, Taejun (KR)

( * ) Notice: Subject to any disclaimer, the term of this patent is extended or adjusted under 35 U.S.C. 154(b) by 0 days.

(21) Appl. No.: 09/533,157

(22) Filed: Mar. 23, 2000

(30) Foreign Application Priority Data

Mar. 23, 1999 (KR) ............................................. 99-9808

(51) Int. Cl.[7] ................................................. G01B 9/02
(52) U.S. Cl. ......................... 356/503; 356/497; 356/517
(58) Field of Search ................................ 356/630, 480, 356/485, 492, 503, 504, 517, 496; 250/559.27, 559.28; 358/497

(56) References Cited

U.S. PATENT DOCUMENTS 5,398,113 A * 3/1995 de Groot .................... 356/497

OTHER PUBLICATIONS de Groot et al.; "Three-dimensional imaging by sub-Nyquist sampling of white-light interfergrams"; Optics Letters vol. 18, No. 17; pp. 1462–1464, Sep. 1, 1993.

Danielson, et al.; "Absolute optical ranging using low coherence interferometry"; Applied Optics vol. 30, No. 21; pp. 2975–2979, Jul. 20, 1991.

* cited by examiner

Primary Examiner—Samuel A. Turner
Assistant Examiner—Patrick Connolly
(74) Attorney, Agent, or Firm—Akin Gump Strauss Hauer & Feld, L.L.P.

(57) ABSTRACT

A method and a recording medium for measuring three-dimensional thickness profile and refractive index of transparent dielectric thin-film with some patterns or not, which is fabricated in the semiconductor and related industrial field, using white-light scanning interferometry is provided.

A method for measuring a thickness profile using white-light scanning interferometry in optical system includes the following steps. A first step is to extracting a phase graph by acquiring an interference signal and performing Fourier transform. A second step is to extracting a mathematical phase graph through modeling of a measurement object. And a third step is to measuring a profile value and a thickness value by applying an optimization technique to an error function determined by using phase values which is acquired from said first step and said second step.

12 Claims, 13 Drawing Sheets

US 6,545,763 B1

METHOD FOR MEASURING A THICKNESS PROFILE AND A REFRACTIVE INDEX USING WHITE-LIGHT SCANNING INTERFEROMETRY AND RECORDING MEDIUM THEREFOR

TECHNICAL FIELD

The invention relates to a method and a recording medium for measuring a thickness profile and a refractive index, more particularly, to a method and a recording medium for measuring three-dimensional thickness profile and refractive index of transparent dielectric thin-film with some patterns or not, which is fabricated in the semiconductor and related industrial field, using white-light scanning interferometry.

BACKGROUND OF THE INVENTION

It is well known that white-light scanning interferometry is useful for measuring three-dimensional profile of patterns such as semiconductor patterns with the size of a few microns or submicrons.

White-light scanning interferometry also has advantages of being capable of measuring a rough surface or a measurement surface having high step height with high resolution by overcoming $2\pi$ phase ambiguity of the conventional phase-shifting interferometry.

The fundamental principle used for measurement using white-light scanning interferometry is utilizing short coherence length characteristics of white-light.

And the principle of the measurement method is that an interference signal appears only when reference light and measurement light, which are split by a beam splitter, have nearly the same optical path difference.

Therefore, observing the interference signal at a measurement point within measurement region, while moving a measurement object in a direction of light axis (optical axis) at minute intervals, for example, a few nanometers, a short interference signal appears at points where each point has the same optical path difference as a reference mirror.

The three-dimensional profile can be measured by extracting points of these interference signals at all measurement points within measurement region.

These researches for white-light scanning interferometry have been actively developed since 1980s.

Generally, white-light interference signal can be expressed as following equation.

$$I = I_{DC} + \gamma \cos \phi \qquad \text{[Equation 1]}$$

In the above equation 1, I is white-light interference signal which is represented by average light intensity of interference signal $I_{DC}$, visibility function $\gamma$, and cosine function.

As amplitude function of interference signal which varies slowly compared to the interference signal's phase variation represented as cosine function, visibility function $\gamma$ is generally expressed as symmetric function such as Gaussian function or polynomial function format and also has many synonyms such, for example, as envelope function, modulation, signal variance, and so on.

In the ideal interference system, the maximum interference signal is occurred at a point, where the optical path difference between reference plane and measurement point is zero. And the point becomes height of the measurement point.

However, there are lots of errors caused by a number of error sources in the actual interference system. Those error sources are phase variation by reflection at a measurement point, an influence of actuation interval in a direction of light axis, frequency characteristics of light source, and so on For this reason, the primary research field for interference measurement method is improving correctness and repetitiousness of measurement value by complementing above mentioned error sources.

Generally, the development of these researches can be classified into three methods.

The first method is determining a point, where visibility of an interference signal is maximum, as measurement value.

The second method is determining measurement value by slope of phase graph per frequency of an interference signal.

The third method is utilizing phase-shifting method and then determining a measurement point.

The detailed and numerous descriptions are disclosed in the article by Kang Min Ku: The study on the surface profile measurement algorithm using white-light scanning interferometry, KAIST, Ph D. thesis (1999).

And one of the commercially widely used methods is phase analysis per frequency (U.S. Pat. No. 5,398,113, Mar. 14, 1995) proposed by Peter De Groot.

The method greatly improved the disadvantages of the conventional methods using visibility function of an interference signal.

Above mentioned disadvantages are including lots of time for calculation, noise sensitive calculation algorithm, influence by frequency of light source, need for moving distance of two or more signal values per one interference signal period to precisely extract visibility function, and so on.

The white-light source was represented as sum of several wavelengths within uniform bandwidth, and the following relationship [equation 2] between profile information and phase variation per frequency was given by considering an interference signal acquired from white-light source as incoherent superposition.

$$\Phi((k)) = 2kh + \phi_o \qquad \text{[Equation 2]}$$

In the above equation 2, k means propagation vector or angular wave number and mathematically represented as $2\pi/\lambda$.

And here, $\lambda$ means optical wavelength of light source and h means profile value of a measurement point and is represented as relative distance value to reference mirror. Also $\phi_o$ is phase variation by surface reflection and is represented by Fresnel equation. And in the case of measuring surface composed of only a single material, the value of $\phi_o$ is constant through the entire measurement region.

It is understood that phase variation value is represented as a simple equation for the propagation vector k and the slope is profile value of the object to be measured from the above equation 2.

However, these all measurement algorithms have the disadvantages of being applied when reflection is occurred only in the surface and the measurement surface is composed of opaque material.

It is generally known that an interference signal is distorted by multiple reflection phenomena in the thin film when dielectric material of a few nanometers or micrometers is deposited on the surface of the measurement plane.

However, in the case of applying a method using conventional visibility function to the interference signal or a method adopting phase-shifting algorithm, the interference signal appears unsymmetrically by the effect of thin film and the maximum visibility may be appeared at a position where the optical path difference is not zero.

And the position can cause measurement errors.

Also, the method using phase variation per frequency leads to the variation of value of above equation 2 according to thickness of the measurement point.

Therefore, above equation 2 is not represented as a simple equation according to the propagation vector any more, and represented as a complex function format, where the non-linear elements are added to the linear elements expressed as an equation of the first degree.

Thus the conventional algorithms have many problems causing serious measurement errors.

SUMMARY OF THE INVENTION

A method and a recording medium for measuring three-dimensional thickness profile and refractive index of transparent dielectric-thin-film with some patterns or not, which is fabricated in the semiconductor and related industrial field, using white-light scanning interferometry is provided.

A method for measuring a thickness profile using white-light scanning interferometry in optical system includes the following steps.
- (a) extracting a phase graph by acquiring an interference signal and performing Fourier transform;
- (b) extracting a mathematical phase graph through modeling of a measurement object; and
- (c) measuring a profile value and a thickness value by applying an optimization technique to an error function determined by using phase values which is acquired from said step (a) and step (b).

Preferably, wherein said step (c) further includes the following steps.
- (d) setting up an error function by using said phase values which is acquired from said step (a) and said step (b);
- (e) determining search start point by setting up search region at an arbitrary measurement point;
- (f) calculating an error function value and a convergence point where said error function value becomes minimum, for each arbitrary search start point;
- (g) setting up said convergence point, which has minimum error function value out of a plurality of search start points for said arbitrary measurement point, as measurement value; and
- (h) determining whether said measurement values are set for all measurement points, and repeatedly performing said step (e), said step (f), and said step (g) if said measurement values are not set.

Preferably, wherein said error function of said step (d) has characteristics of using said phase value $\Phi^m(k)$ acquired from said step (a) and said phase value $\Phi^c(k)$ of a model acquired from said step (b) and expressed as following equation.

$$\chi^2 = \sum_k [\Phi^m(k) - \Phi^c(k; h, d)]^2$$

Where, k and h means a propagation vector and a configuration value, respectively and d is thickness value of thin film constituting thin film structure.

More preferably, wherein said optimization technique, which is utilized to detect said profile and said thickness values, characterizes utilizing nonlinear least square method in said step (c).

Preferably, wherein said optimization technique, which is utilized to detect said profile and said thickness values, characterizes utilizing nonlinear least square method of Levenberg-Marquardt in said step (c).

A recording medium readable with computer in which program for measuring a thickness profile using white-light scanning interferometry is provided. The program includes the following steps.
- (a) extracting a phase graph by acquiring an interference signal and performing Fourier transform;
- (b) extracting a mathematical phase graph through modeling of a measurement object; and
- (c) measuring a profile value and a thickness value by applying an optimization technique to an error function determined by using phase values which is acquired from said step (a) and said step (b).

A method for measuring a refractive index using white-light scanning interferometry in optical system is provided. The method includes the following steps.
- (a) extracting a phase graph by acquiring an interference signal and performing Fourier transform;
- (b) extracting a mathematical phase graph through modeling of a measurement object; and
- (c) measuring a refractive index by applying an optimization technique to an error function determined by using phase values which is acquired from said step (a) and said step (b).

Preferably, wherein said step (c) further includes the following steps.
- (d) setting up an error function by using said phase value which is acquired from said step (a) and said step (b);
- (e) determining search start point by setting up search region at an arbitrary measurement point;
- (f) calculating an error function value and a convergence point where said error function value becomes minimum, for each arbitrary search start point;
- (g) setting up said convergence point, which has minimum error function value out of a plurality of search start points for said arbitrary measurement point, as a measurement value; and
- (h) determining whether said measurement values are set up for all measurement points, and repeatedly performing said step (e), said step (f), and said step (g).

More preferably, wherein said error function of said step (d) has characteristics of using said phase value $\Phi^m(k)$ acquired from said step (a) and said phase value $\Phi^c(k)$ of a model acquired from said step (b) and expressed as following equation.

$$\chi^2 = \sum_k [\Phi^m(k) - \Phi^c(k; N_i)]^2$$

Where, k means a wave number and $N_i$ means a refractive index of thin film constituting thin film structure.

Preferably, wherein said optimization technique, which is utilized to detect said refractive index, characterizes utilizing nonlinear least square method in said step (c).

More preferably, wherein said optimization technique, which is utilized to detect said refractive index, characterizes utilizing nonlinear least square method of Levenberg-Marquardt in said step (c).

A recording medium readable with computer in which program for measuring a refractive index using white-light scanning interferometry is provided. The program includes the following steps.
- (a) extracting a phase graph by acquiring an interference signal and performing Fourier transform;
- (b) extracting a mathematical phase graph through modeling of a measurement object; and (c) measuring a refractive index by applying optimization technique to said error function determined by using said phase value which is acquired from said step (a) and said step (b).

BRIEF DESCRIPTION OF THE DRAWINGS

The embodiments of the present invention will be explained with reference to the accompanying drawings, in which.

DETAILED DESCRIPTION OF THE INVENTION

Figure 1:
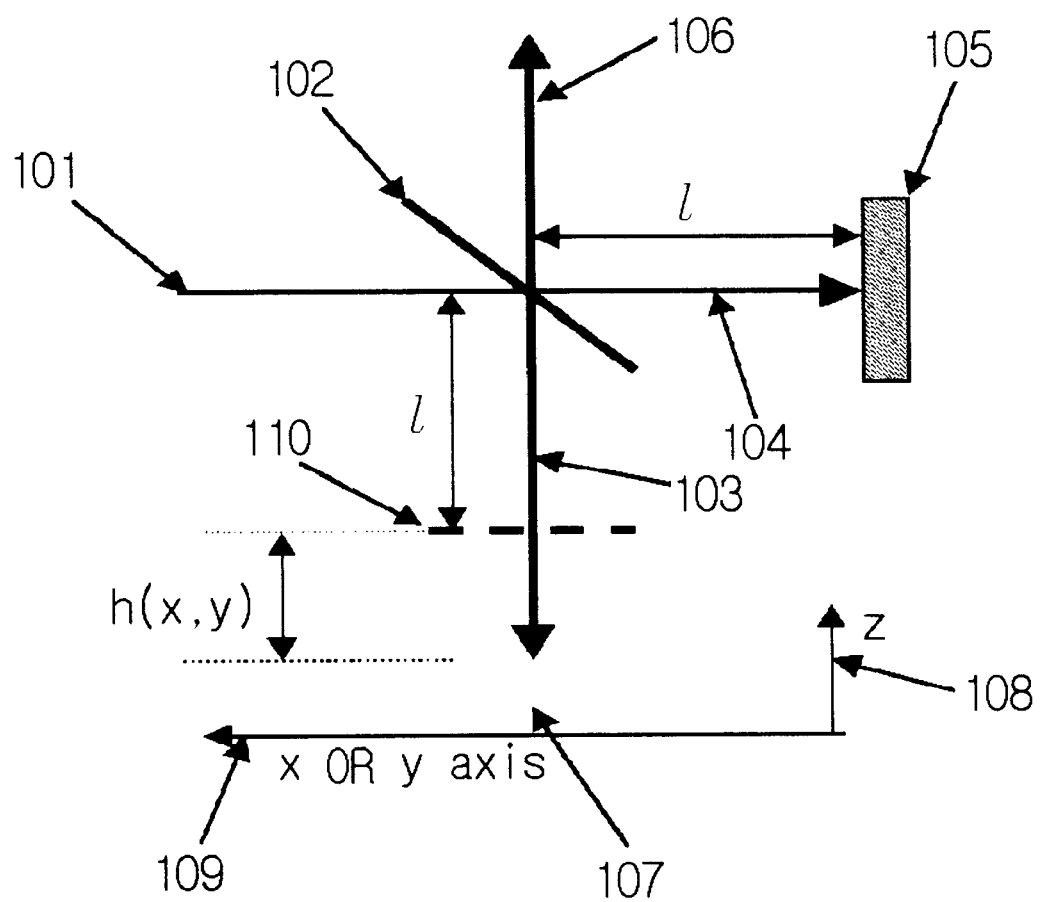
FIG. 1 is an explanatory drawing of the principle of white-light scanning interferometry.

Details of measurement method of three-dimensional thickness profile and refractive index and an agreeable demonstration example for an apparatus according to the invention are well described below.

The physical research of multiple reflection and related phenomena in the thin film has been actively developed.

The overall and general contents are well described in the article by R. M. A. AZZAM and N. M. BASHARA entitled "Ellipsometry and Polarized Light (North-Holland, Amsterdam, 1987)".

However, in the case of an opaque material in which only surface reflection appears, phase variation of reflected light to incidence light is represented mathematically by utilizing Fresnel equation.

These phase variation can be classified into two classes according to polarized constituents of light source and represented by incidence angle of light source and two complex refractive indexes constituting boundary plane.

Considering only normal incidence of light source, incidence angle of light source above described is zero in general measurement.

Therefore, phase variation by surface reflection is represented as a function of only complex refractive indexes of two materials constituting boundary plane.

And because material of measurement plane generally can be known, the conventional algorithms consider phase variation as constant value.

However, in the case of transparent thin film being deposited on the surface one portion of incidence light is reflected on the surface and the other portions penetrates into the thin film.

The penetrated light again reflected on the boundary plane between substrate and the thin film.

In that case, the reflected light proceeds in a direction of the boundary plane between an incidence medium and a thin film and reaches a boundary plane, then forms reflected light proceeding into the thin film and the penetrated light from the incidence medium.

By using those methods, incidence light theoretically makes penetration and reflection infinitively, and then the reflected light in final thin film is represented as mathematical sum of all lights which proceeds in the opposite direction of the incidence light out of several lights which was described above.

The present invention determines total reflection coefficient similar to the Fresnel's reflection coefficients to mathematically analyze those reflected lights.

The total reflection value in one layer thin film structure of incidence medium-thin film-substrate is expressed as following equation 3.

$$R = \frac{r_{01} + r_{12}e^{-j2\beta}}{1 + r_{01}r_{12}e^{-j2\beta}} \quad \text{[Equation 3]}$$

In the above equation 3, $r_{01}$ and $r_{02}$ represents the Fresnel's reflection coefficients of the boundary plane of incidence medium-thin film, and of thin film-substrate, respectively.

$\beta$ means suffered phase variation of light proceeding into the thin film from one boundary plane to the other boundary plane, and mathematically represented as $\beta = 2dN_1\cos\theta_1$, where d, $N_1$, and $\theta_1$ mean thickness of the thin film, complex refractive index, and proceeding angle of light in thin film, respectively.

In the above equation 3, because total reflection index R has complex value, it determines amplitude variation of reflected light and phase variation.

The above described multiple reflection phenomena is occurred complicatedly in the structures having one or more layer thin film. Therefore scattering matrix is defined and then utilized to analyze those phenomena.

The scattering matrix is a characteristic matrix to determine the relationship of light distribution between arbitrary two points within thin film and can be represented as following equation 4.

$$\begin{bmatrix} E^+(z_1) \\ E^-(z_1) \end{bmatrix} = \begin{bmatrix} S_{11} & S_{12} \\ S_{21} & S_{22} \end{bmatrix} \begin{bmatrix} E^+(z_2) \\ E^-(z_2) \end{bmatrix} \quad \text{[Equation 4]}$$

$z_1$ and $z_2$ mean arbitrary two points in the thin film and E+ is light intensity which has the same direction as incidence light in the thin film and E− is light intensity proceeding in the opposite direction.

Each element $S_{ij}$ of scattering matrix is represented by the Fresnel's reflection and penetration index, phase variation $\beta$ suffered while penetrating the thin film, and so on.

By utilizing the scattering matrix, total reflection index is mathematically expressed as equation 5.

$$R = \frac{S_{21}}{S_{11}} \quad \text{[Equation 5]}$$

In the case of applying to thin film with one layer, the same result can be obtained as that from equation 3 by utilizing equation 5.

Furthermore the phase variation in the thin film can be represented as equation 6 by utilizing above equation 3 or equation 5.

$$\psi(k, d) = \angle R \quad \text{[Equation 6]}$$

Considering the phase variation in the thin film represented as above equation 6, the white-light interference signal is expressed as follows.

In the drawings, FIG. 1 is an explanatory drawing of the principle of white-light scanning interferometry.

Referring to FIG. 1, white-light 101 whose bandwidth is from $k_1$ to $k_2$ is split to measurement light 103 and reference light 104 by a beam splitter 102.

The reference light 104 is reflected at a reference mirror 105 and then projected into the beam splitter 102 through the same path.

The measurement light 103 is projected into the beam splitter 102 after reflected from a measurement object 107.

The summed light at the beam splitter 102 forms an interference signal 106 and is detected by the detector.

In FIG. 1, number 110 represents a point that has the same distance as the reference mirror 105.

As drawn in FIG. 1, the profile information h(x, y) is defined as a distance to the measurement point from the point (1 1 0) which is at the same distance as the reference mirror 105.

Here, x- or y-axis is determined as a direction perpendicular to z-axis.

And the white-light interference signal is obtained by detecting the interference signal 106 while moving the measurement object 107 in a direction of z-axis.

Also, it is assumed that the measurement object 107 is composed of homogeneous materials and has optically isotropic characteristics and incidence light is projected into the measurement plane perpendicularly as shown in FIG. 1.

From the condition above described, the white-light interference signal obtained is modeled as equation 7.

$$i^w(z) = \int_{k_1}^{k_2} i_0(k, d)[1 + \gamma(k, d) \cos[2k(h-z) + \psi(k, d)]] F(k) dk \quad \text{[Equation 7]}$$

In above equation 7, $i_0(k, d)$ and $\gamma(k, d)$ means average light intensity of the interference signal and visibility function respectively, and F(k) is frequency profile function of the white-light.

And the x and y coordinates were omitted for the sake of convenience in the above equation 7.

The superscript w means the white-light and k means propagation vector, and d is thickness of thin film.

The fundamental assumption for the above equation 7 is incoherent superposition of light sources with single frequency which consist of white-light as described above.

Therefore, the phase of light sources with single frequency which was obtained from equation 7 can be modeled as following equation 8.

$$\Phi^c(k) = 2kh + \psi(k, d) \quad \text{[Equation 8]}$$

From the consideration of above equation 8, it is understood that the phase variation of light with single wavelength, which occurs in thin film structure is represented as sum of linear phase variation 2kh that was occurred from the distance difference between the measurement point and the reference mirror 105 shown in FIG. 1 and nonlinear phase variation $\psi(k, d)$ in the thin film.

Therefore, profile information h of the measurement point and thickness value d can be determined as mathematical models shown as equation 8 by analyzing actually measured phase value per wavelength.

However, the h and d cannot be determined mathematically because the phase variation $\psi(k, d)$ is represented as nonlinear equation like equation 3 or 5 in thin film.

In the present invention, the optimization technique, which performs curve fitting the modeled equation 8 to the actually measured value, is utilized to produce profile value and thickness value.

The method performs the measured phase curve fitting, while varying the h and d value of the above equation 8 in the actually measured phase curve.

Here, when the most similar graph to the actual phase graph was obtained, the h and d value is determined as the profile and the phase value in the measurement point.

In the case of utilizing the optimization technique, an error function which estimates a degree of curve fitting is needed and the error function is determined as equation 9.

$$\chi^2 = \sum_k [\Phi^m(k) - \Phi^c(k; h, d)]^2 \quad \text{[Equation 9]}$$

The $\Phi^m(k)$ means phase value which is obtained from the actual white-light interference signal according to wavelength.

The error function expressed as above equation 9 is determined as square sum of the difference between the $\Phi^m(k)$, which is measured phase value of each wavelength at an arbitrary point h and d, and modeled value 101 $^c(k)$.

As described above, the value of h and d at the point that makes $\chi^2$ be minimum is determined as the profile value and the thickness value at that measurement point.

By using above equation 9 several optimization techniques can be applied, and in most cases it converges to optimal value.

The Levenberg-Marquardt nonlinear least square method out of the optimization techniques is utilized in the invention.

And the fast convergence rate within 20 times was proved by experimenting with the method.

However, in the case of applying the nonlinear least square method above described, the local minimum problem which may have several convergence points according to positions of an initial examination points.

Those local minimum problems can be solved by determining search region in which true values may exist and by setting several points in search region as search start points and then by determining a convergence point with a minimum value as the measurement value after searching all convergence points.

By the method described above, the profile value and the thickness value can be obtained at each measurement point for all measurement points in two-dimensional measurement region.

And exact three-dimensional thickness profile of minute submicron-sized pattern in transparent isolated layer thin film that was impossible to be measured by the conventional method, can be measured by the method.

FIG. 2A to FIG. 2D are simplified drawings of the semiconductor patterns' surface profile that can be constructed actually.

Figure 2A:
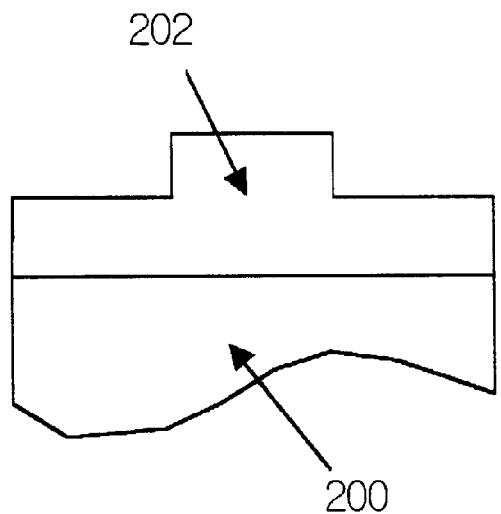
FIG. 2A to FIG. 2D are simplified drawings of semiconductor patterns' surface profile that can be constructed actually.

FIG. 2A is a case of depositing a transparent isolated layer 202 on a plain substrate 200.

Figure 2B:
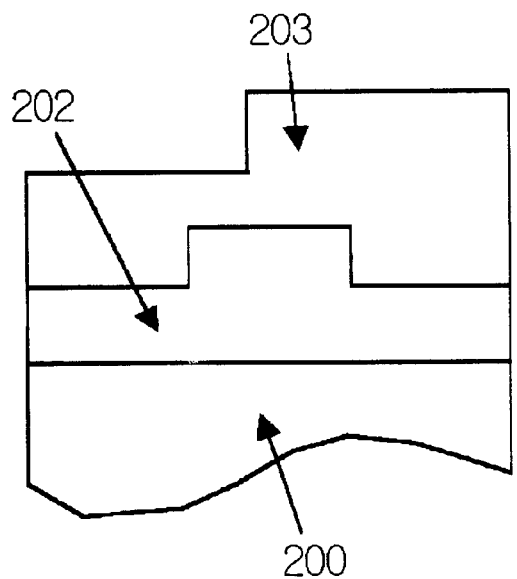

FIG. 2B is a case of depositing a thin film with inhomogeneous or homogeneous material 203 on that shown in FIG. 2A.

Several thin film layers can be deposited by these methods.

Figure 2C:
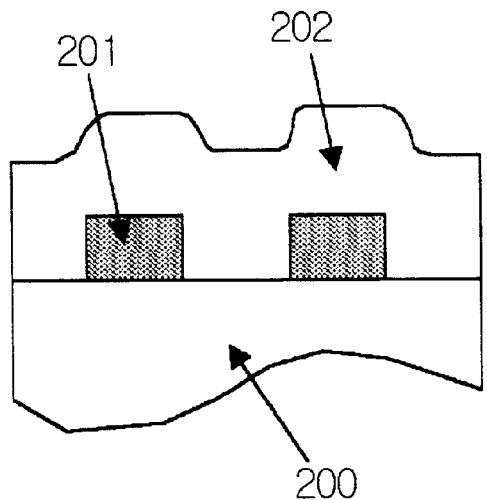

FIG. 2C is a case of that a metal layer is constructed on a plain substrate 200 and a transparent isolated layer 202 is deposited on the metal layer.

Figure 2D:
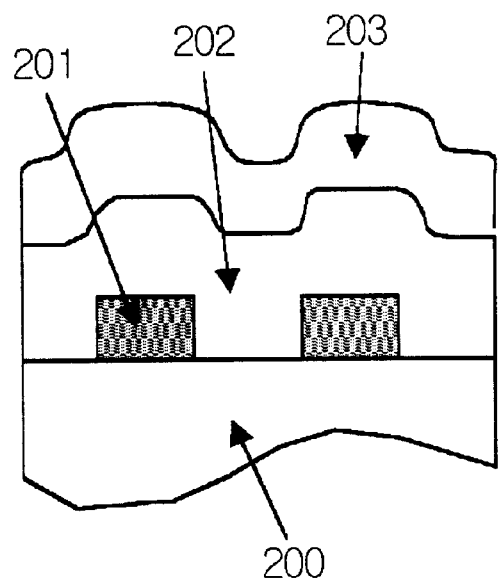

FIG. 2D is a case of depositing a thin film with inhomogeneous or homogeneous material 203 on that shown in FIG. 2C.

Also, in these cases several thin film layers can be deposited by these methods.

As described above, FIG. 2A to FIG. 2D exemplifies cases that are measurable and the algorithm that is proposed in the invention can be applied to all cases of transparent thin films being constructed.

Figure 3A:
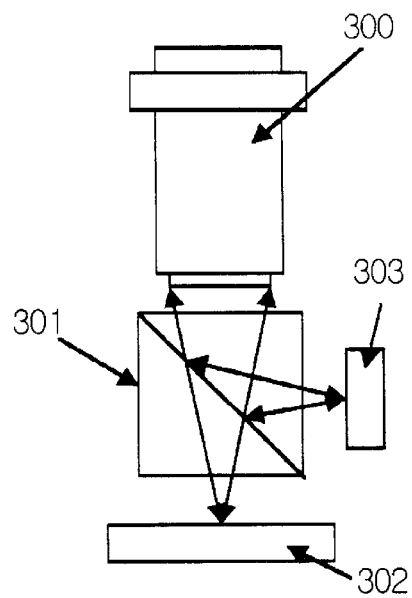
FIG. 3A to FIG. 3C are drawings of an optical interferometry system utilized in the present invention.
Figure 3B:
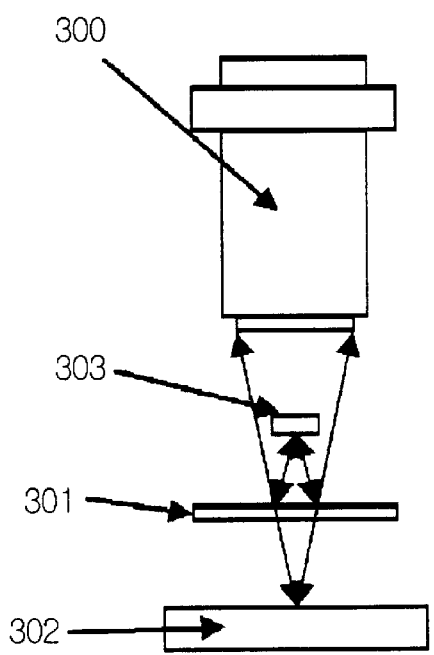
Figure 3C:
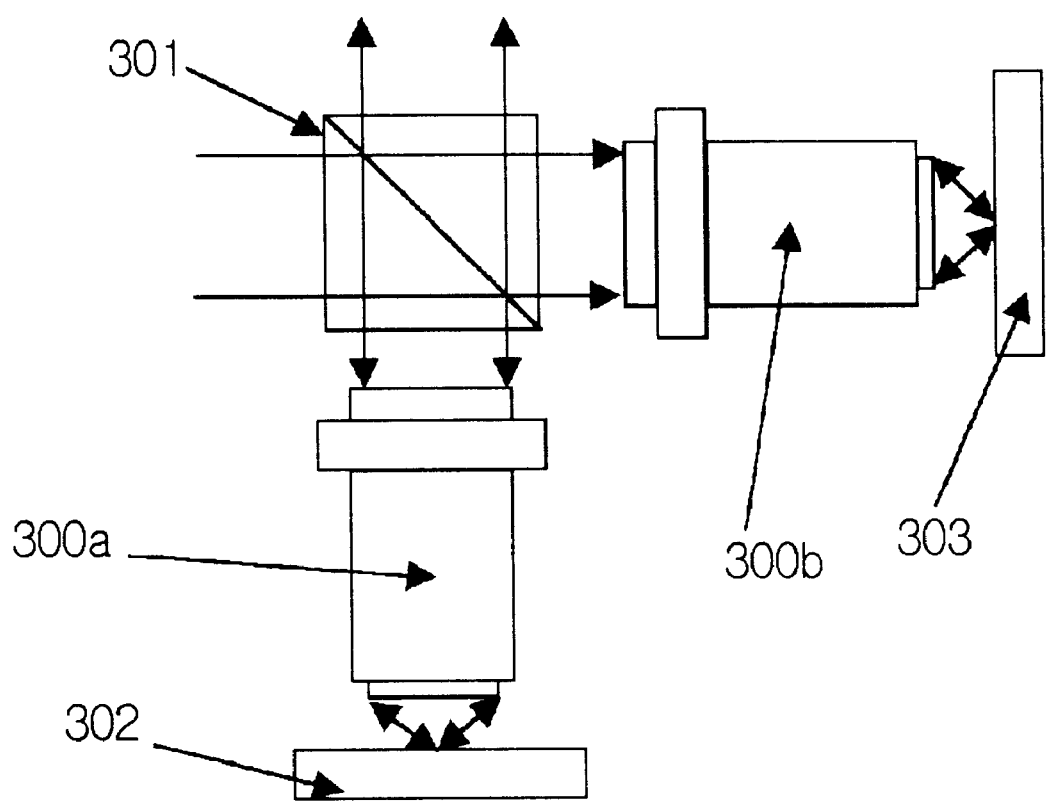

FIG. 3A to FIG. 3C are drawings of optical interferometry system utilized in the present invention.

FIG. 3A shows the Michelson interferometry where a beam splitter 301 splitting measurement light and reference light is built in the front part of an objective lens 300 and a reference mirror 303 and a measurement object 302 is also built there.

FIG. 3B is the Mirau interferometry where a reference mirror 303, a beam splitter 301 and a measurement object 302 are built in the front part of the objective lens 300.

FIG. 3C exemplifies the Linnik interferometry, where a beam splitter 301 splits measurement light and reference light and the reference light is reflected from a reference mirror 303 after penetrating an objective lens 300 and the measurement light forms an interference signal together with the reference light after being projected on a measurement object 302 by a objective lens 300a.

As described above, a measurement method of the present invention can be applied to all interferometries, which are exemplified in FIG. 3A to FIG. 3C. And the present invention utilizes the Mirau interferometry shown in FIG. 3B.

Figure 4:
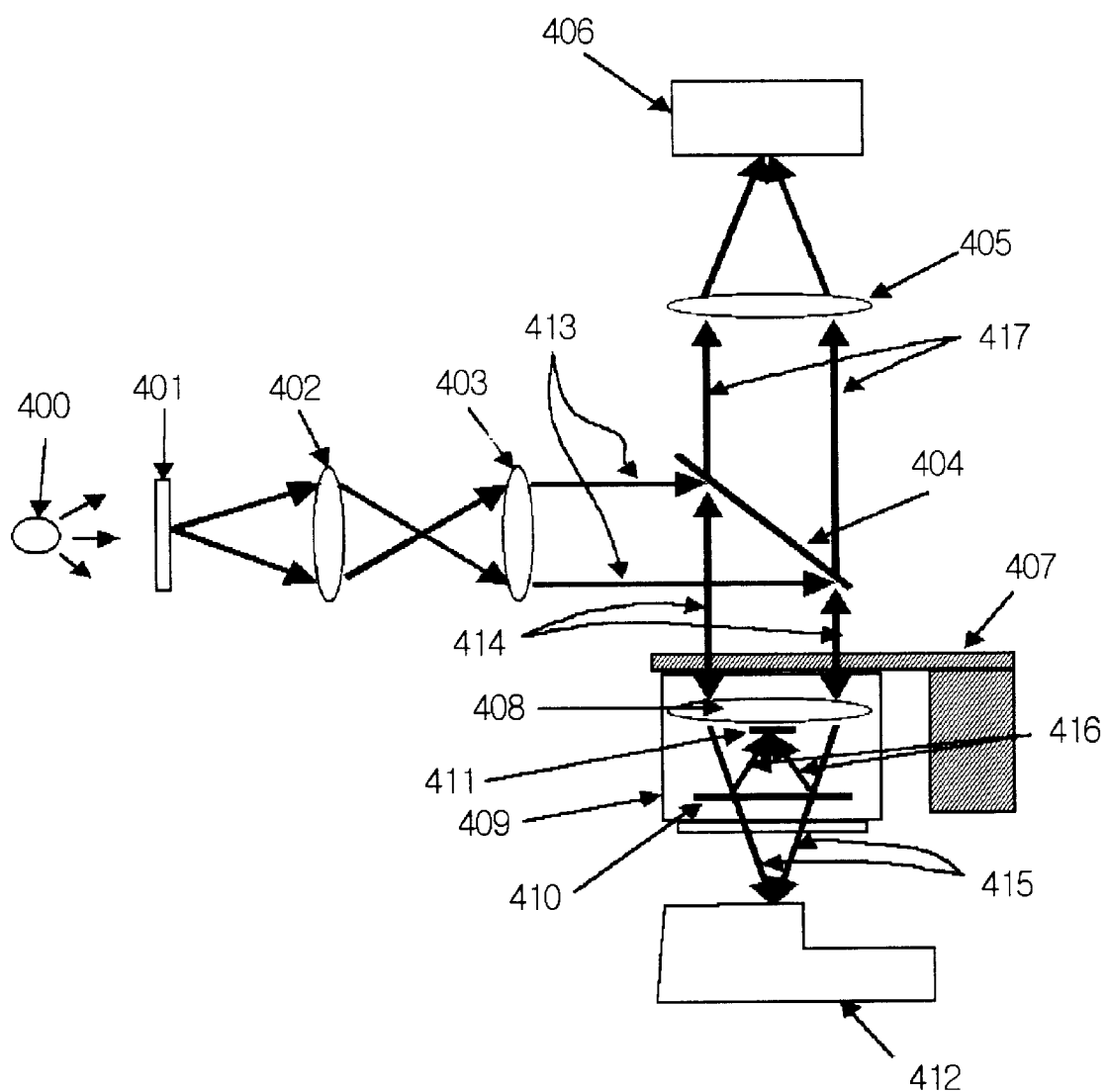
FIG. 4 is a diagrammatic drawing of an optical system of Mirau interferometry applied to the present invention.

FIG. 4 is a diagrammatic drawing of an optical system of Mirau interferometry applied to the present invention.

The Mirau interferometry being applied to the present invention has a white-light source 400 and here, the 100 W halogen lamp is used as a white-light source 400.

Also, the Mirau interferometry also has a Neutral density filter 401 which is used only to reduce brightness without changing spectrum characteristics of incidence light projected from the white-light source 400.

Furthermore, this interferometry also has a condenser lens 402 to collect light from the neutral density filter 401.

And the Mirau interferometry has a collimator lens 403 to make parallel light which has penetrated the condenser lens 402.

Still furthermore the optical system of the Mirau interferometry splits the light which has penetrated the collimator lens 403 into reflection light and penetration light, and then the split reflection light is projected onto the backside of an objective lens 408. Also the optical system has a beam splitter 404 for penetrating the incidence light. Here, the beam splitter 404 used has a ratio of 50 to 50 for reflexibility and transmissivity, respectively.

Also, the optical system of the Mirau interferometry projects the split reflected light, which has been incident from the beam splitter 404, onto measurement plane and has a objective lens 408 for penetrating the interference light being incident.

The penetrated light from the objective lens 408 is split into reflected light and penetrated light and then the penetrated light is made to be incident into the measurement plane as a measurement light 415 in an optical system of the Mirau interferometry.

Also, the optical system of the Mirau interferometry makes the reflected light be projected onto a reference mirror 411 as reference light 416 and has a beam splitter 410 in order to make interference light by gathering the reference light 416, which has been reflected from the reference mirror 411 and the measurement light 415, which has been reflected from a measurement object 412.

And the optical system of the Mirau interferometry has the reference mirror 411 in order that the reflected reference light from the beam splitter 410 is incident into the beam splitter 410.

Furthermore the optical system of the Mirau interferometry has an image formation lens 405 which makes the incident interference light 417, which is incident from the beam splitter 404, as an image.

Still furthermore, the optical system has the reference mirror 411 in order that reference light 416, which is incident from the beam splitter 410 is incident into the beam splitter 410.

There is a detector 406 for detecting the interference signal from the interference light in the optical system. A CCD (Charge Coupled Device) camera with 768×494 pixels is used for the detector 406.

And in the Mirau interferometry system the piezoelectric actuator 407 was utilized to obtain the interference signal while moving measurement point in a direction of optical axis at minute intervals.

While, because a body tube 409 is built in the piezoelectric actuator 407, moving the piezoelectric actuator 407 makes the objective lens 408 move in a direction of z-axis.

When the objective lens 408 is moved in the up and down direction of the focus at intervals of a few tens of nanometers, the most intensive interference signal is occurred at the measurement point of the CCD camera, which have the same optical path as the beam splitter 410 as described above.

Figure 5:
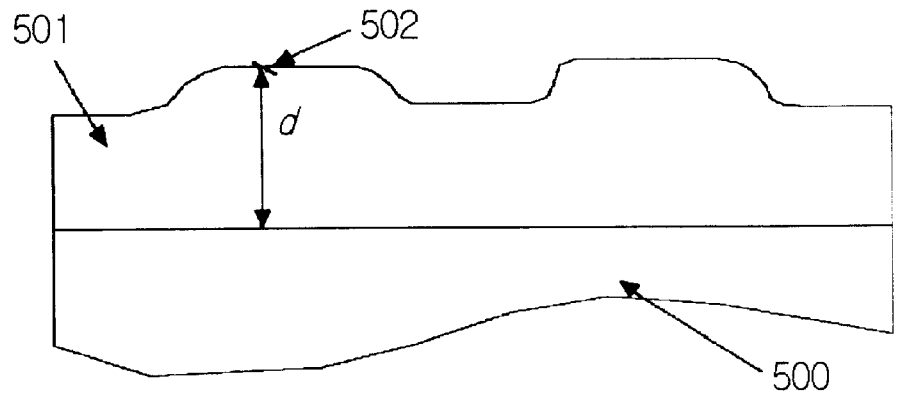
FIG. 5 is a cross section of a sample applied to the present invention.

FIG. 5 is a cross section of a sample applied to the present invention.

The cross sectional structure of the sample used in the experiment has deposited $SiO_2$ (silicon dioxide) 501 with some patterns on flat silicon 500 as drawn in FIG. 5.

Figure 6:
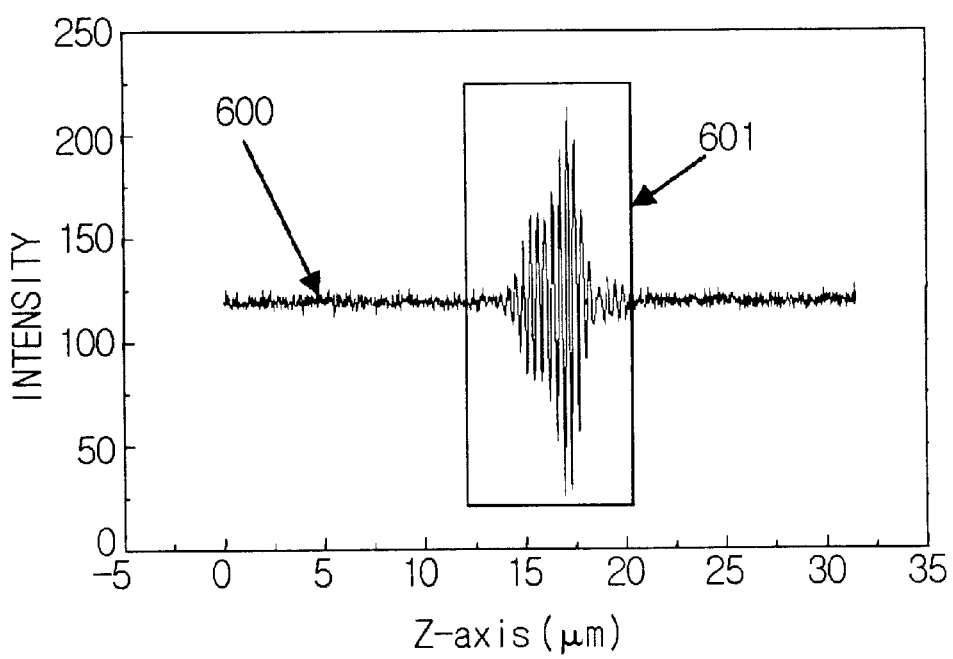
FIG. 6 is a graph depicting a measured interference signal of the sample shown in FIG. 5 using the interferometry shown in FIG. 4.

The interference signal 600 shown in FIG. 6 is obtained by obtaining an interference signal at an arbitrary point 502 having thickness d using the Mirau interferometry system shown in FIG. 4.

FIG. 6 is a graph depicting a measured interference signal of the sample shown in FIG. 5 using the interferometry shown in FIG. 4.

As shown in FIG. 6 an intensive interference signal 601 is occurred at the position of the focus, and only noises are occurred at the other positions.

By observing the interference signal 601, it is known that the interference signal is unsymmetrical as described above. The Fourier transform is utilized to extract the phase value per optical frequency.

For doing so, $2^N$s' data are acquired to include the interference signals 601 sufficiently, where N is an integer.

Figure 7:
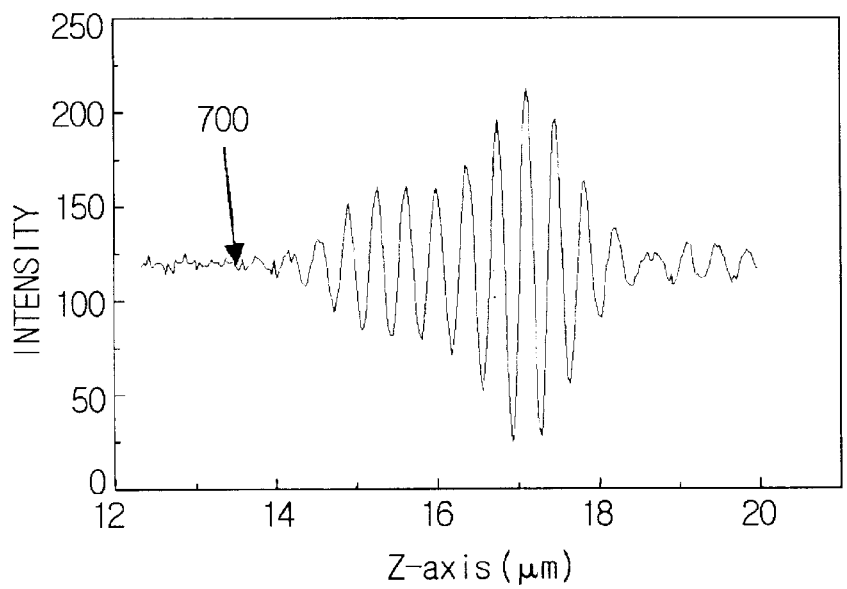
FIG. 7 is a graph depicting 256 data acquired from the interference signals shown in FIG. 6.

FIG. 7 is a graph depicting 256s' data acquired from the interference signals shown in FIG. 6.

Figure 8:
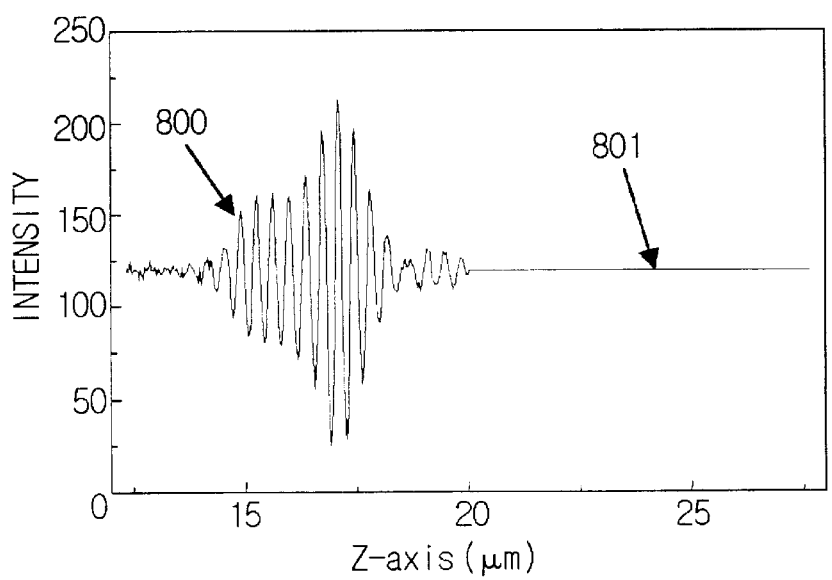
FIG. 8 is a graph depicting a result from adding 256 average light intensity values of the interference signal to an existent signal.

FIG. 8 is a graph depicting a result from adding average light intensity value of the interference signal to an existent signal.

Figure 9:
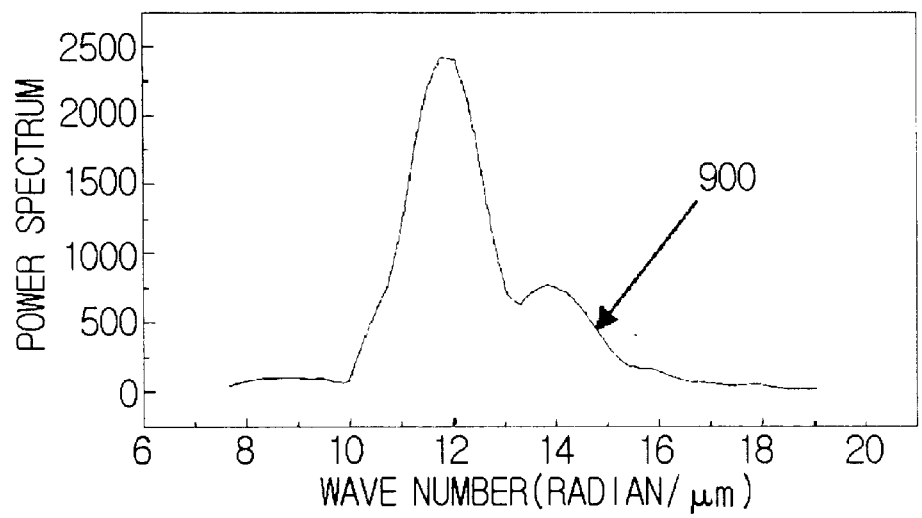
FIG. 9 is a graph depicting a power spectrum curve for acquired frequencies which are resulted from performing Fourier transform of the interference signals shown in FIG. 8.

FIG. 9 is a graph depicting a power spectrum curve for the acquired frequencies which are resulted from performing Fourier transform of the interference signals shown in FIG. 8.

Figure 10:
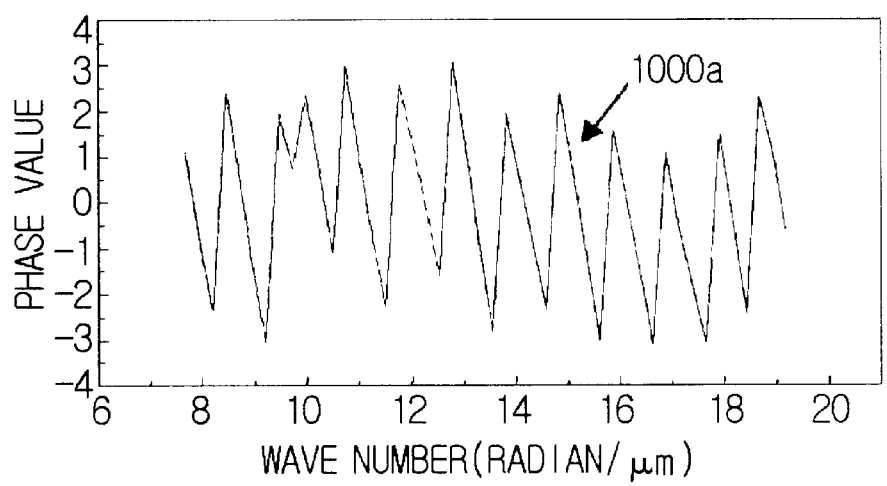
FIG. 10 is a graph depicting a phase value curve for acquired frequencies which are resulted from performing Fourier transform of the interference signals shown in FIG. 8.

FIG. 10 is a graph depicting a phase value curve for the acquired frequencies which are resulted from performing Fourier transform of the interference signals shown in FIG. 8.

Figure 11:
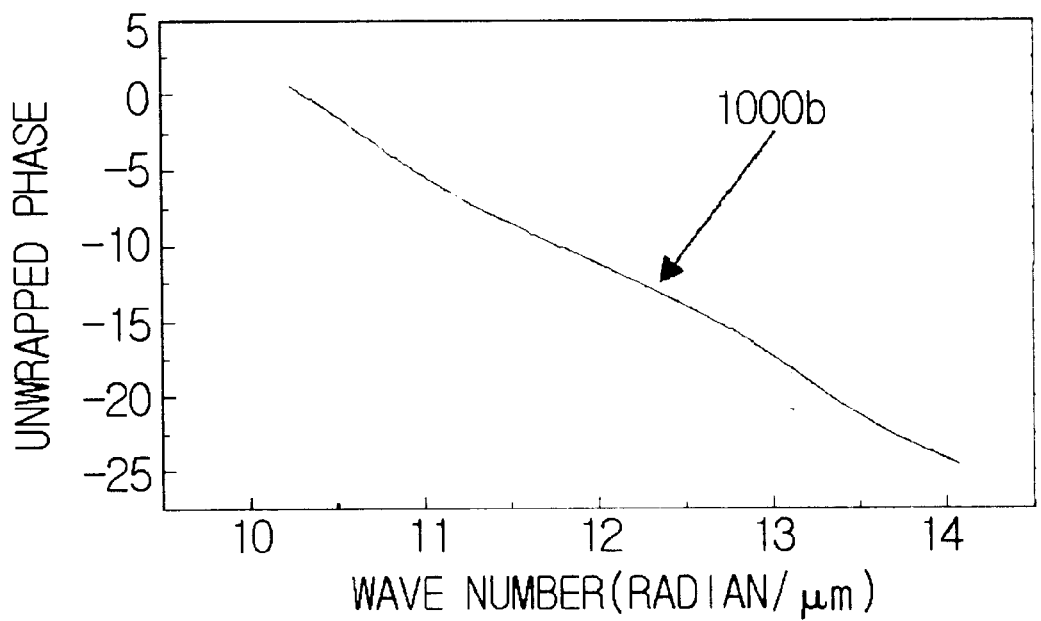
FIG. 11 is a graph depicting an unwrapped phase curve when unwrapping the phase value curve shown in FIG. 10.

FIG. 11 is a graph depicting an unwrapped phase curve when unwrapping the phase value curve shown in FIG. 10.

The new interference signal is made by adding an average value 801 of light intensity to the interference signal shown in FIG. 6 so many as the number of interference signals selected from FIG. 7.

FIG. 8 shows a newly made interference signal.

A power spectrum per frequency 900 of an interference signal such as FIG. 9 and a phase value per frequency 1000a in the FIG. 10 can be obtained by performing Fourier transform of the newly made interference signal. The frequency of the interference signal is correspondent to propagation vector or wave number.

And, an unwrapped phase graph 1000b shown in FIG. 11 can be obtained by unwrapping only power spectrum values beyond threshold value shown in FIG. 10.

By considering an unwrapped phase graph 1000b, it is seen that the graph is not linear and nonlinear elements are included by the effect of the thin film.

And data 1000b shown in FIG. 11 is correspondent to $\phi_m(k)$ of above equation 9.

As minutely described above, after determining a mathematical phase model such as above equation 8 and an error function of above equation 9, apply the nonlinear least square method of Levenberg-Marquardt and vary profile value and thickness value in order to make error function be minimum.

Figure 12A:
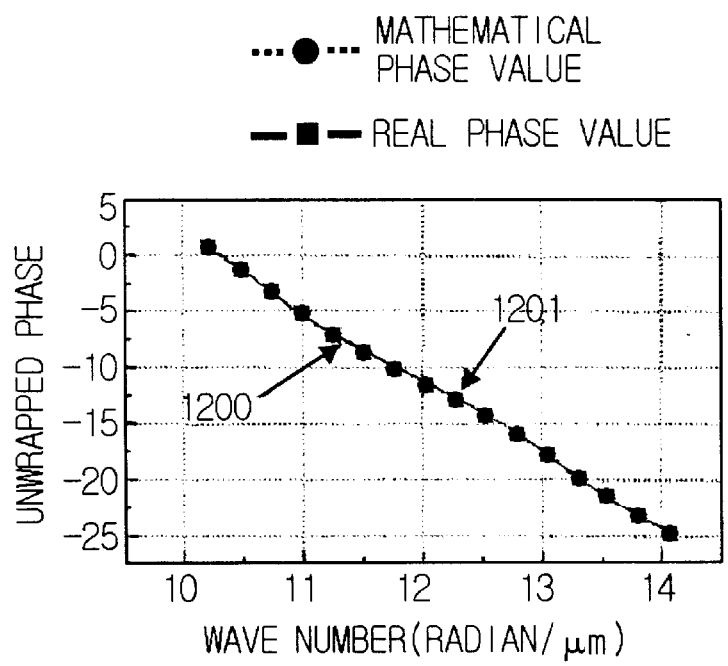
FIG. 12A and FIG. 12B are graphs depicting comparisons between actual phase graph and mathematical phase graph in the case of minimum convergence of error function.
Figure 12B:
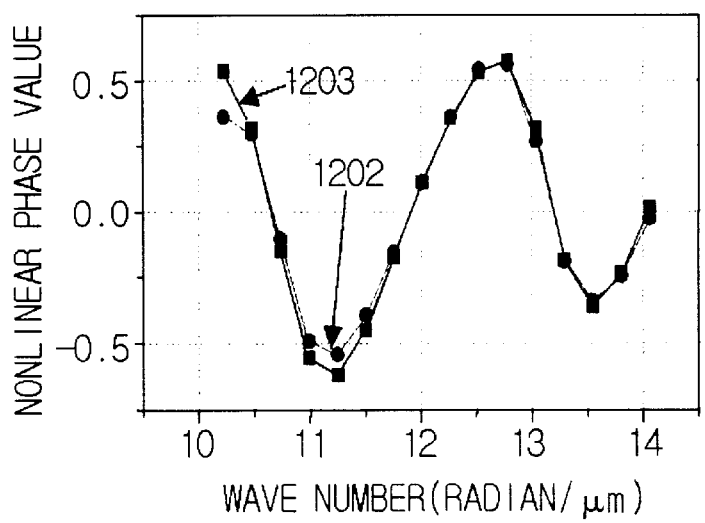

FIG. 12A and FIG. 12B are graphs depicting comparisons between actual phase graph and mathematical phase graph in the case of minimum convergence of error function.

It is seen that the actual phase graph 1200 and the mathematical phase graph 1201 is almost the same as that shown in FIG. 12A.

Also, it is known that FIG. 12B, where the linear element of the FIG. 12A was eliminated, is entirely similar to FIG. 12A except for some errors.

Therefore, it is proved that the mathematical phase model, which was determined by equation 8, is reasonable.

Figure 13:
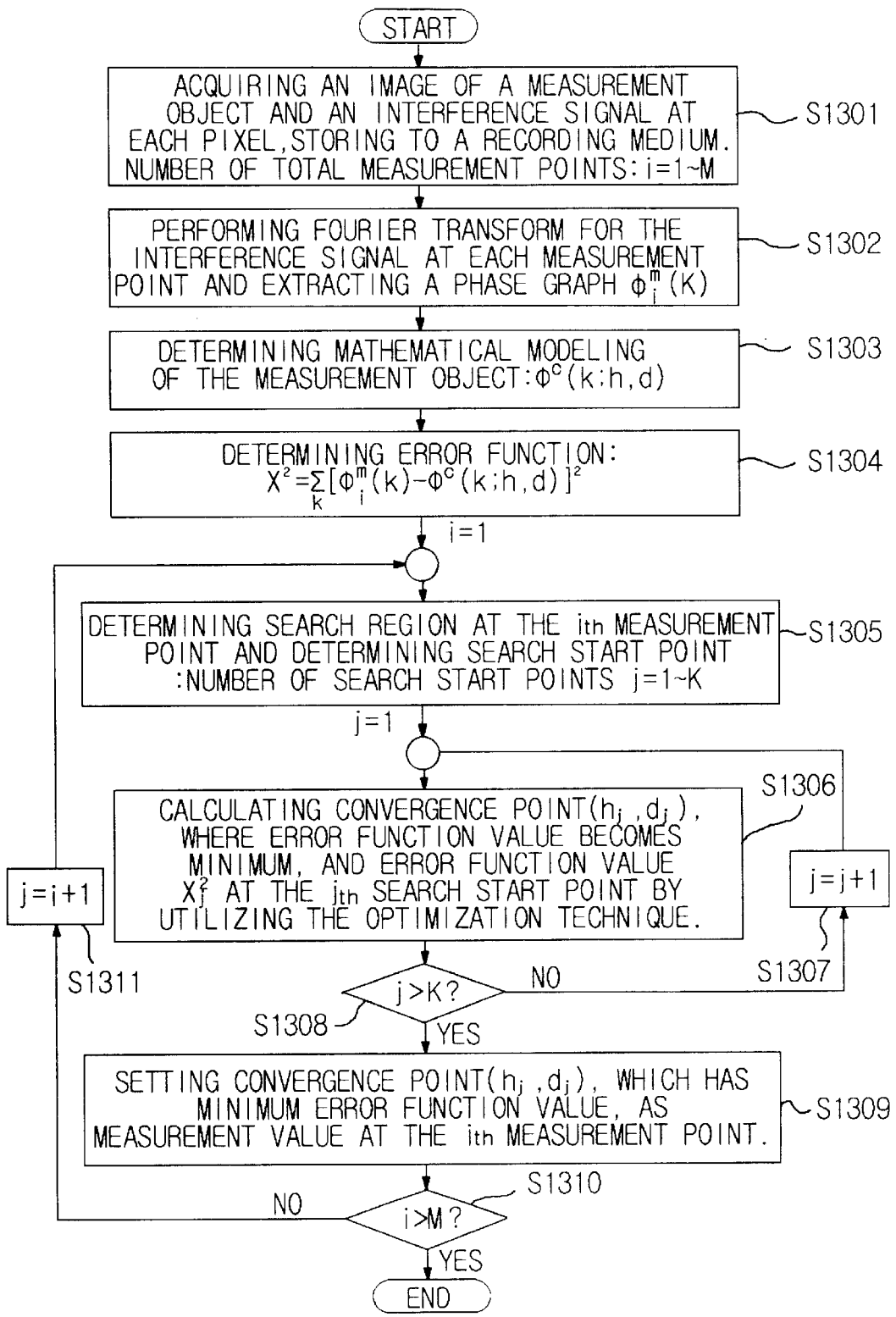
FIG. 13 is a flow chart depicting a measurement method for three-dimensional thickness profile of a transparent dielectric thin film using white-light scanning interferometry as a demonstrating example of the present invention.

FIG. 13 is a flow chart depicting a measurement method for three-dimensional thickness profile of a transparent dielectric thin film using white-light scanning interferometry as a demonstrating example of the present invention.

As shown in FIG. 13, the measurement method for three-dimensional thickness profile of a transparent dielectric thin film using white-light scanning interferometry according to an example of the present invention is as follows.

First, in step S1301, after acquiring an image of a measurement object within measurement region and an interference signal of each pixel, store those in the recording medium. Here, it is assumed that the total measurement number (expressed as i in the followings) is M.

The detector used here is what is capable of obtaining two-dimensional image and composed of a plurality of pixels and each pixel of the detector is correspondent to the measurement position of a measurement object.

And the interference signal means intensity variation graph of the interference signal per pixel, which has been obtained by moving the distance between reference plane and measurement plane at minute intervals.

These interference signals are different from each other by profile of measurement plane or thickness.

And in step S1302, a phase graph is obtained by performing Fourier transform of acquired interference signal.

In step S1303, determine a model for the measurement object, which has thin film structure, and in step S1304, the error function is determined and i is set as 1, where i means measurement position.

Next, in step S1305, search region for the $i_{th}$ measurement position is determined and search start point (expressed as j in the followings) is also determined, where the number of search start points is assumed as k.

And, in step S1306, convergence point, where error function becomes minimum, and the value of the error function is calculated by using the optimization technique at the jth search start point.

And in step S1308, judge whether convergence point and error function were calculated for all search start points. If not, plus one to the j and redo from the step S1306. If convergence point and error function were calculated for all search start points, set convergence point for search start point, which has the least error function out of calculated error functions, as measurement value of the $i_{th}$ measurement point.

And in step S1310, judge whether measurement values were solved at all measurement points. If not, increment i by one in step S1311 and redo from the step S1305. If all measurement values for all measurement points were solved, finish the measurement.

While, the optimization algorithm, which is utilized in the step S1306, may be either the nonlinear least square method or the nonlinear least square method of Levenberg-Marquardt.

Figure 14:
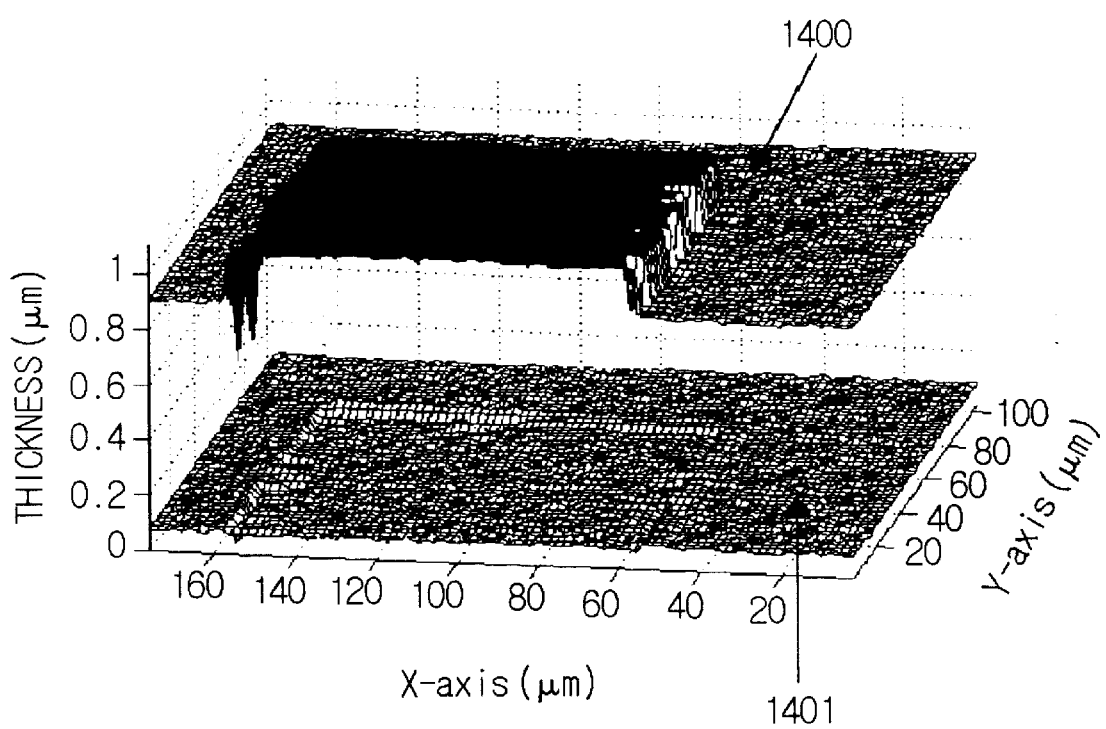
FIG. 14 is an isometric representation depicting the results of the thickness profile of a $SiO_2$ thin film by utilizing the present invention.

FIG. 14 is an isometric representation depicting results of thickness profile of an $SiO_2$ (Silicon Dioxide) thin film by utilizing the present invention.

As shown in FIG. 14, the result of the thickness profile of an $SiO_2$ thin film is a measurement object having deposited artificial $SiO_2$ layer 1400 on the plain silicon substrate 1401.

The size of emerged pattern is 100 $\mu$m×100 $\mu$m and thickness is about 1.1 $\mu$m as shown in FIG. 14.

The thickness of natural part is about 0.8 $\mu$m.

By the present invention the profile measurement of transparent isolated surface, which was impossible to be measured by the conventional methods, was enabled and minute thickness variation, which was also impossible by the conventional methods, was measured at the same time.

Therefore, there is an advantage that three-dimensional thickness profile of transparent isolated layer with some patterns can be measured through the present invention.

Although FIG. 14 was applied to a thin film structure with a single layer, a thin film structure with two or more layers can be applied by the same method.

And the measurement method for three-dimensional thickness profile of transparent thin film layer using white-light scanning interferometry in the invention is capable of measuring the refractive index of thin film within visible range in the case of knowing thickness of thin film exactly.

Although the measurement method for three-dimensional thickness profile of transparent thin film layer using white-light scanning interferometry in the present invention set refractive index of thin film as known value, and then measured thickness and surface profile at measurement position, the refractive index of the thin film can be solved by the same optimization method upon the assumption that thickness and profile values are known.

The detailed explanation of above description is as follows.

As the method for measuring complex refractive index of each layer and three-dimensional thickness of thin film constituting transparent structure, the present invention includes following measurement steps.

- (a) The illuminated light from light source makes an interference signal after being projected onto reference plane and measurement plane, and then reflected respectively and a detector acquires an interference signal. The detector used is what consists of a plurality of pixels, which can acquire two-dimensional images. Each pixel of the detector is correspondent to each measurement point in the measurement plane.
- (b) While moving the distance between the measurement plane and the reference plane at minute intervals, the intensity variation of the interference signal is stored per pixel. The intensity variation-graph of the interference signal, which is finally stored in one pixel, is called as the interference signal. These interference signals are different per each pixel according to measurement plane.
- (c) The interference signal at each pixel, which was obtained in the step (b), is transformed into a signal in spatial frequency region. After transforming, the phase values in spatial frequency region, which have power spectrum beyond the threshold, are phase unwrapped.
- (d) Determine a mathematical model of thin film on the measurement object. The mathematical model includes surface profile and thickness value and refractive index value of each layer, which constitute a thin film, as variables. The mathematical phase curve, that is, modeled phase curve is extracted by these values.
- (e) Determine error function by using the phase values obtained from the step (c) and step (d).
- (f) By applying the optimization technique to the error function, which was determined in step e, search values of refractive indexes, that make the error function become minimum.
- (g) By performing the step f for all pixels of the detector, measure the refractive index per pixel.

In addition, wherein step (e) has following detailed sub-steps.

- (i) The actually measured phase value and mathematically modeled phase value are expressed as a function of wave number or propagation vector.
- (ii) The error function is expressed as a relative equation of the phase values, which are correspondent to the same wave number in the actual and modeled phase values.

Also, above described step (f) has following detailed sub-steps.

- (1) Determine the range of refractive index value at a measurement point to be searched as search region.
- (2) Determine search start point at regular intervals within search region.
- (3) Calculates the convergence point according to each search start point by utilizing the optimization searching technique.
- (4) The convergence point, which has the least error function value out of a plurality of convergence points calculated from step (3), is set as the measurement value at the related measurement point.

The nonlinear least square method is used in order to search for convergence point of the error function.

And nonlinear least square method of Levenberg-Marquardt is utilized in step (3) in order to search for convergence point of the error function.

And in step (ii), the error function is represented as equation 10.

$$x^2 = \sum_k ([\Phi^m(k) - \Phi^c(k; N_i)])^2 \qquad \text{[Equation 10]}$$

Above equation 10 determines error function as square sum of differences between phase values corresponding to the same wave number in the actual and modeled phase graph.

In the above equation 10, k means wave number and $N_i$ is refractive index value of a thin film constituting thin film structure.

In the above step (g), the profile of refractive index at each measurement point also can be unwrapped.

While, the applicable interferometries in step (a) include Mirau, Linnik, Michelson, and so on.

What is claimed is:

1. A method for measuring a thickness profile using white-light scanning interferometry in optical system, comprising the steps of:
    (a) extracting a phase graph by acquiring an interference signal and performing Fourier transform;
    (b) extracting a mathematical phase graph through modeling of a measurement object; and
    (c) measuring a profile value and a thickness value by applying an optimization technique to an error function determined by using phase values which is acquired from said step (a) and said step (b).

2. The method for measuring the thickness profile according to claim 1, wherein said step (c) further comprises:
    (d) setting up an error function by using said phase values which is acquired from the said step (a) and said step (b);
    (e) determining search start point by setting up search region at an arbitrary measurement point;
    (f) calculating an error function value and a convergence point where said, error function value becomes minimum, for each arbitrary search start point;
    (g) setting up said convergence point, which has minimum error function value out of a plurality of search start points for said arbitrary measurement point, as measurement value; and
    (h) determining whether said measurement values are set for all measurement points, and repeatedly performing said step (e), said step (f), and said step (g) if said measurement value are not set.

3. The method for measuring the thickness profile according to claim 2, wherein said error function of said step (d) has characteristics of using said phase value $\Phi^m(k)$ acquired from said step (a) and said phase value $\Phi^c(k)$ of a model acquired from said step (b) and expressed as following equation.

$$\chi^2 = \sum_k [\Phi^m(k) - \Phi^c(k; h, d)]^2$$

Where, k and h means a propagation vector and a configuration value, respectively and d is thickness value of thin film constituting thin film structure.

4. The method for measuring the thickness profile according to claim 3, wherein said optimization technique, which is utilized to detect said profile and said thickness values, characterizes utilizing nonlinear least square method in said step (c).

5. The method for measuring the thickness profile according to claim 3, wherein said optimization technique, which is utilized to detect said profile and said thickness values, characterizes utilizing nonlinear least square method of Levenberg-Marquardt in said step (c).

6. A recording medium readable with computer in which program for measuring a thickness profile using white-light scanning interferometry, wherein said program comprises the steps of:
   (a) extracting a phase graph by acquiring an interference signal and performing Fourier transform;
   (b) extracting a mathematical phase graph through modeling of a measurement object; and
   (c) measuring a profile value and a thickness value by applying an optimization technique to an error function determined by using phase values which is acquired from said step (a) and said step (b).

7. A method for measuring a refractive index using white-light scanning interferometry in optical system, comprising the steps of:
   (a) extracting a phase graph by acquiring an interference signal and performing Fourier transform;
   (b) extracting a mathematical phase graph through modeling of a measurement object; and
   (c) measuring a refractive index by applying an optimization technique to an error function determined by using phase values which is acquired from said step (a) and said step (b).

8. The method measuring the refractive index according to claim 7, wherein said step (c) further comprises:
   (d) setting up an error function by using said phase value which is acquired from said step (a) and said step (b);
   (e) determining search start point by setting up search region at an arbitrary measurement point;
   (f) calculating an error function value and a convergence point where said error function value becomes minimum, for each arbitrary search start point;
   (g) setting up said convergence point, which has minimum error function value out of a plurality of search start points for said arbitrary measurement point, as a measurement value; and
   (h) determining whether said measurement values are set up for all measurement points, and repeatedly performing said step (e), said step (f), and said step (g).

9. The method measuring the refractive index according to claim 8, wherein said error function of said step (d) has characteristics of using said phase value $\Phi^m(k)$ acquired from said step (a) and said phase value $\Phi^c(k)$ of a model acquired from said step (b) and expressed as following equation.

$$\chi^2 = \sum_k [\Phi^m(k) - \Phi^c(k; N_i)]^2$$

Where, k means a wave number and $N_i$ means a refractive index of thin film constituting thin film structure.

10. The method measuring the refractive index according to claim 9, wherein said optimization technique, which is utilized to detect said refractive index, characterizes utilizing nonlinear least square method in said step (c).

11. The method measuring the refractive index according to claim 9, wherein said optimization technique, which is utilized to detect said refractive index, characterizes utilizing nonlinear least square method of Levenberg-Marquardt in said step (c).

12. A recording medium readable with computer in which program for measuring a refractive index using white-light scanning interferometry, wherein said program comprises the steps of:
   (a) extracting a phase graph by acquiring an interference signal and performing Fourier transform;
   (b) extracting a mathematical phase graph through modeling of a measurement object; and
   (c) measuring a refractive index by applying optimization technique to said error function determined by using said phase value which is acquired from said step (a) and said step (b).

* * * * *